United States Patent [19]

Villari et al.

[11] Patent Number: 4,699,155
[45] Date of Patent: Oct. 13, 1987

[54] URINE METER WITH CORRUGATED TUBE

[75] Inventors: Frank K. Villari, Oak Park; Carl J. Steigerwald, Wauconda, both of Ill.

[73] Assignee: The Kendall Company, Boston, Mass.

[21] Appl. No.: 302,926

[22] Filed: Sep. 16, 1981

[51] Int. Cl.⁴ .................... A61B 19/00; A61M 1/00
[52] U.S. Cl. .................................... 128/762; 604/318
[58] Field of Search ............. 128/276, 295, 760, 767, 128/DIG. 24; 138/121, 173; 604/317, 318

[56] References Cited

U.S. PATENT DOCUMENTS

| 3,683,894 | 8/1972 | Villari | 128/767 |
| 4,095,589 | 6/1978 | Manschot | 128/295 |
| 4,305,404 | 12/1981 | Dunn | 128/767 |

FOREIGN PATENT DOCUMENTS

| 1220975 | 1/1971 | United Kingdom | 138/173 |
| 1391027 | 4/1975 | United Kingdom | 138/121 |

OTHER PUBLICATIONS

"Convoluted", Random House Dictionary, The Unabridged Edition, New York, N.Y., 1966, p. 320.

Primary Examiner—C. Fred Rosenbaum
Assistant Examiner—J. L. Kruter
Attorney, Agent, or Firm—Powell L. Sprunger

[57] ABSTRACT

A urine meter comprising, a container having a cavity for collection of urine, and a drainage tube for draining urine from a patient. The urine meter has a receptacle having a chamber, with the drainage tube communicating with an upper portion of the receptacle for passage of urine into the chamber. The urine meter has a conduit of flexible material communicating between an upper portion of the receptacle and an upper portion of the container, with the conduit having a curve from the container to the receptacle, an outer corrugated wall, and an inner smooth wall. The receptacle is releasably supported on a front side of the container.

4 Claims, 6 Drawing Figures

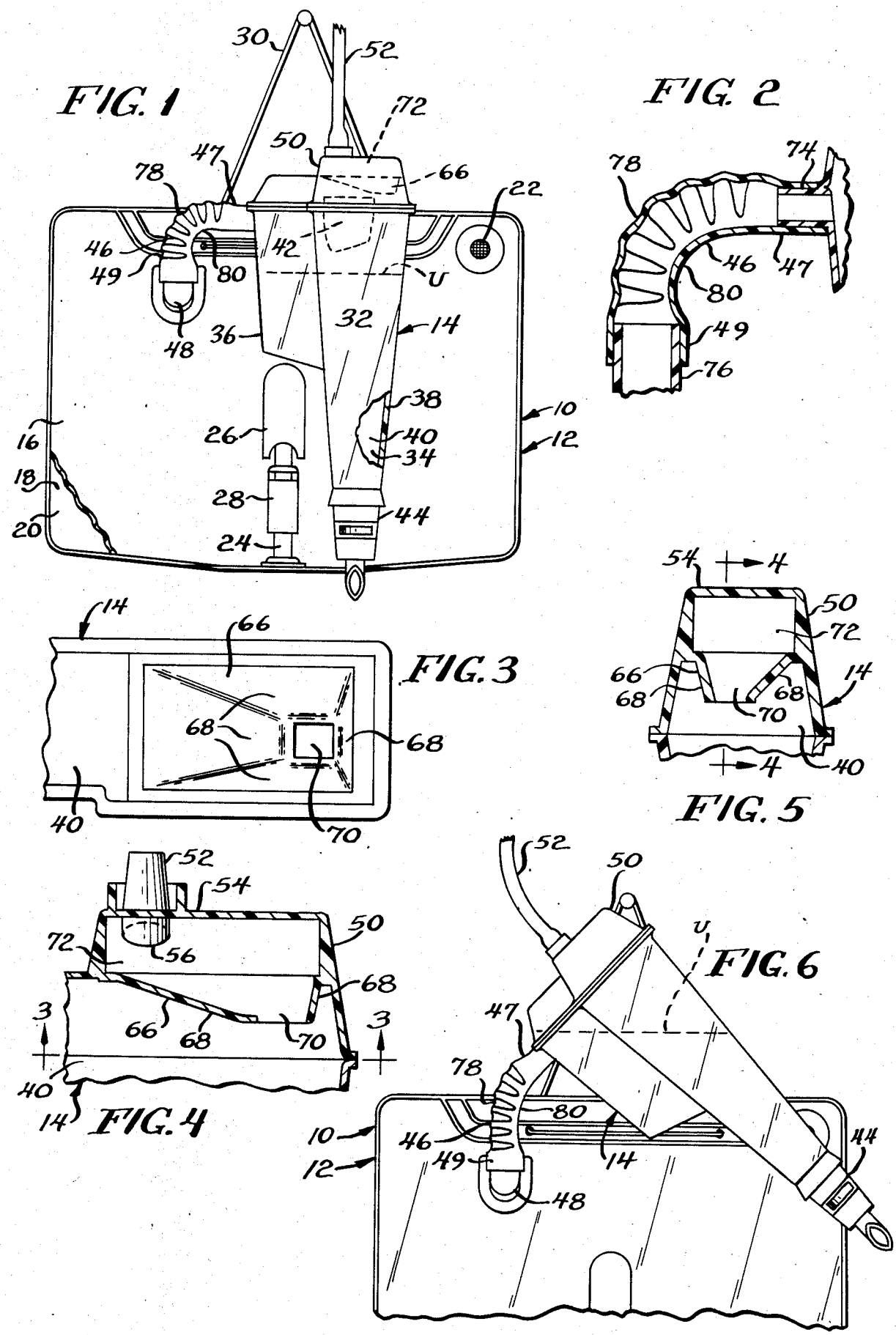

ary sectional view of a lower portion of the baffle and the receptacle; and

FIG. 6 is a fragmentary front plan view of the urine meter showing the receptacle being tilted to pass urine into a container of the urine meter.

URINE METER WITH CORRUGATED TUBE

BACKGROUND OF THE INVENTION

The present invention relates to urine receptacles, and more particularly to urine meters.

Before the present invention, urine meters have been proposed of the type having a container, a receptacle, and a drainage tube communicating with an upper portion of the receptacle. The receptacle may be used to determine incoming urine volumes with relative accuracy, and the receptacle may be periodically emptied into the container where the urine is stored. However, it is desirable to remove a vent from the receptacle, which was previously required when emptying the receptacle into the container, since the vent adds cost to the urine meter.

SUMMARY OF THE INVENTION

A principal feature of the present invention is the provision of an improved urine meter for receiving urine from a patient.

The urine meter of the present invention comprises, a container having a cavity for collection of urine, and a drainage tube for draining urine from a patient. The urine meter has a receptacle having a chamber, with the drainage tube communicating with an upper portion of the receptacle for passage of urine into the chamber. The urine meter has a conduit of flexible material communicating between an upper portion of the receptacle and an upper portion of the container, with the conduit having a curve from the container to the receptacle, an outer corrugated wall, and an inner smooth wall. The urine meter has means for releasably supporting the receptable in a first upright position on a front side of the container.

A feature of the present invention is that the receptacle is moved to a second tilted position to empty the contents of the receptacle through the conduit into the container.

Another feature of the invention is that the conduit has a sufficiently large diameter to permit passage of air through the conduit when the receptacle is being emptied in the second position to eliminate the necessity of a vent on the receptacle.

Still another feature of the invention is that the curved conduit eliminates kinking of the relatively large conduit in the first position of the receptacle.

Yet another feature of the invention is that the corrugated wall of the conduit prevents kinking of the conduit when the receptacle is moved to the second tilted position.

Further features will become more fully apparent in the following description of the embodiments of this invention and from the appended claims.

DESCRIPTION OF THE DRAWINGS

In the drawings:

FIG. 1 is a fragmentary front plan view of a urine meter of the present invention;

FIG. 2 is a fragmentary sectional view of the conduit for the urine meter of FIG. 1;

FIG. 3 is a lower plan view of a baffle on a receptacle of the urine meter taken substantially as indicated along the line 3—3 of FIG. 4;

FIG. 4 is a fragmentary sectional view taken substantially as indicated along the line 4—4 of FIG. 5;

FIG. 5 is a fragmentary sectional view of a lower portion of the baffle and the receptacle; and FIG. 6 is a fragmentary front plan view of the urine meter showing the receptacle being tilted to pass urine into a container of the urine meter.

DESCRIPTION OF THE PREFERRED EMBODIMENTS

Referring now to FIG. 1, there is shown a urine meter generally designated 10 having a container 12 and a receptacle 14. The container 12 has a front wall 16 and a rear wall 18 of flexible material, such as a suitable plastic, being joined together around the periphery thereof and defining a cavity 20 between the front and rear walls 16 and 18. The front wall 16 of the container 12 has a vent 22 with a bacteria filter of known type communicating with the container cavity 20. The container 12 has a tubular section 24 communicating with a lower portion of the cavity 20, and having an outer end removably received in a pocket 26, with the tubular section 24 having a releasable clamp 28 on the tubular section. Thus, when it is desirable to drain urine from the container 12, the tubular section 24 is removed from the pocket 26, and the clamp 28 is released to permit passage of urine through the tubular section 24. The container 12 also has a string 30 attached to an upper portion of the container 12 to permit hanging of the urine meter 10 from a suitable object during use. The container 12 has a connector 48 attached to the front wall 16 and communicating with the cavity 20.

With reference to FIGS. 1-5, the receptacle 14 has a front wall 32, a rear wall 34, and a pair of side walls 36 and 38 defining a chamber 40 in the receptacle 14. The receptacle 14 has a hook 42 extending from the rear wall 34 and spaced from the rear wall 34 to receive an upper portion of the container 12 in order to support the receptacle 14 in a first upright position on the upper portion of the container 12. The receptacle 14 has a lower valve 44 to permit draining of urine when desired from the receptacle chamber 40 to obtain a specimen of urine. The urine meter 10 has a flexible conduit 46 having one end 47 connected to the receptacle 14 adjacent the side wall 36 such that it communicates with an upper portion of the chamber 40, and the other end 49 of the conduit 46 is attached by the connector 48 to an upper portion of the container 12 on the front wall 16, such that the conduit 46 communicates with an upper portion of the cavity 20. Thus, the conduit 46 communicates between an upper portion of the chamber 40 and an upper portion of the cavity 20 for a purpose which will be described below.

As shown, the receptacle 14 has a raised portion 50 adjacent an upper end of the receptacle 14. The urine meter 10 has a drainage tube 52 for draining urine from the patient, with a downstream end of the drainage tube 52 extending through an upper wall 54 of the raised portion 50 into the receptacle 14 to define a drip tube 56 inside the receptacle 14. As shown, the receptacle 14 has a baffle 66 extending across the lower part of the raised portion 50, with the baffle 66 having downwardly sloping walls 68 defining a lower opening 70 adjacent the side wall 38. The baffle 66 defines a compartment 72 in the raised portion 50, with the drip tube 56 being located in the compartment 72 above the walls 68 of the baffle 66.

As best shown in FIG. 2, the receptacle 14 has a tubular section 74 extending from an upper part of the side wall 36 of the receptacle 14, with the tubular section 74 being received in the one end 47 of the conduit 46. Also, the connector 48 has a tubular section 76 received in the other end 49 of the conduit 46, with the tubular sections 74 and 76 holding the conduit 46 in place. The conduit 46 is formed in a natural curved state, such that the conduit 46 is curved from the connector 48 of the container 12 to the upper part of the receptacle 14. The curved conduit 46 prevents kinking of the conduit 46 when the receptacle 14 is in its first upright position, as shown in FIG. 1. With reference to FIG. 2, the conduit 46 has an outer corrugation wall 78, and an inner smooth wall 80. The conduit 46 may be formed of any suitable plastic material, such as polyvinylchloride, and may be formed in a suitable manner, such as dip molding, slush molding, blow molding, or rotational molding.

In use, urine drains from a catheter (not shown) in the patient through the drainage tube 56 into the compartment 72, where it drains along the wall 68 of the baffle 66 through the opening 70 into the receptacle chamber 40. As the urine collects in the chamber 40 of the receptacle 14, the volume of urine may be determined by suitable indicia (not shown) on the front wall 32 of the receptacle 14. When a suitable volume of urine U has been collected in the receptacle chamber 40, as shown in FIG. 1, the urine U may be emptied into the container 12 for retention therein.

In order to accomplish this result, the receptacle 14 is lifted from the container 12 to remove the hook 42 from the upper portion of the container 12, and the receptacle is moved to a second tilted position, as shown in FIG. 6, such that urine U passes through the conduit 46 and connector 48 into the cavity 20 of the container 12. In this manner, the urine U is transferred from the receptacle 14 to the container 12 in order to initiate collection of a new volume of urine in the receptacle 14. Also, the urine U may be permitted to overflow from the receptacle 14 through the conduit 46 into the container 12 during collection of urine. When the receptacle 14 is tilted to pass urine into the container 12, the baffle 66 prevents passage of urine into the drip tube 56 in the event that the receptacle 14 is tilted too far during the emptying procedure. Also, when the receptacle is placed in the second tilted position, the outer corrugated wall 78 prevents kinking of the conduit 46 in order to prevent blockage of urine in the conduit 46. The conduit 46 has a sufficiently large diameter to permit passage of air through the conduit 46 when the receptacle 14 is placed in the second tilted position, such that a vent on the receptacle 14 may be eliminated to reduce cost of the urine meter 10 to the patient.

The foregoing detailed description is given for clearness of understanding only, and no unnecessary limitations should be understood therefrom, as modifications will be obvious to those skilled in the art.

We claim:

1. A urine meter, comprising:
   a container having a cavity for collection of urine;
   a drainage tube for draining urine from a patient;
   a receptacle having a chamber, with the drainage tube communicating with an upper portion of the receptacle for passage of urine into the chamber;
   a conduit of flexible material communicating between an upper portion of the receptacle and an upper portion of the container, said conduit having a curve from the container to the receptacle, an outer circumferential wall portion relative to the receptacle having outer and inner corrugated surfaces, and an inner circumferential wall portion relative to the receptacle having outer and inner smooth wall surfaces; and
   means for releasably supporting the receptacle in a first upright position on a front side of the container, said receptable being moved to a second tilted position to empty the contents of the receptacle through the conduit into the container.

2. The meter of claim 1 wherein the supporting means comprises a hook extending from a rear portion of the receptacle for placement over an upper portion of the container.

3. The meter of claim 1 including a connector attached to the front wall of the container and communicating with the cavity, said connector having a tubular section received in one end of the conduit.

4. The meter of claim 1 wherein the receptacle has a tubular section on one side of the receptacle received in one end of the conduit.

* * * * *